(12) United States Patent
Shtarov et al.

(10) Patent No.: US 7,572,942 B2
(45) Date of Patent: Aug. 11, 2009

(54) SYNTHESIS OF CARBON-LABELED PERFLUOROALKYL COMPOUNDS

(75) Inventors: Alexander Borisovich Shtarov, Wilmington, DE (US); Jon Lee Howell, Bear, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/001,269

(22) Filed: Dec. 11, 2007

(65) Prior Publication Data

US 2008/0097131 A1    Apr. 24, 2008

Related U.S. Application Data

(62) Division of application No. 10/794,556, filed on Mar. 5, 2004, now Pat. No. 7,351,870.

(51) Int. Cl.
C07C 19/08    (2006.01)

(52) U.S. Cl. ..................................... 570/134
(58) Field of Classification Search .............. 570/134
See application file for complete search history.

(56) References Cited

U.S. PATENT DOCUMENTS

| | | | |
|---|---|---|---|
| 3,250,808 A | 5/1966 | Moore, Jr. et al. | |
| 4,400,325 A * | 8/1983 | von Werner et al. | 423/500 |
| 4,874,557 A | 10/1989 | Kruse et al. | |
| 4,940,814 A * | 7/1990 | Schwertfeger | 562/849 |
| 5,399,754 A | 3/1995 | Oyama et al. | |
| 6,653,511 B2 | 11/2003 | Howell et al. | |
| 2002/0042521 A1* | 4/2002 | Sonoda et al. | 548/300.1 |
| 2003/0013922 A1 | 1/2003 | Howell et al. | |
| 2003/0013924 A1* | 1/2003 | Howell et al. | 568/677 |

FOREIGN PATENT DOCUMENTS

| | | |
|---|---|---|
| EP | 0367256 | 5/1990 |
| JP | 52 053813 A | 4/1977 |
| JP | 2002322269 A | 11/2002 |
| WO | WO 95/16656 | 6/1995 |

OTHER PUBLICATIONS

Seleznev, V.G. et al, *Photolysis of 1-14C-perfluoropropyl iodide by powerful light pulses*, Zhurnal Organicheskoi Khimii, 12(2) 266-9; Coden: Zorkae; ISSN: 0514-7492, 1976.

Gauri S. Lal et al., *Bis(2-methoxyethyl)aminosulfur Trifluoride: A New Broad-Spectrum Deoxofluorinating Agent with Enhanced Thermal Stability*, J. Org. Chem. 1999, 64, 7048-7054.

V. G. Seleznev, et al., *J. Org. Chem.*, USSR (Eng. Translation), 12, 1976, 259.

M. Haddach et al., *J. Labelled Comp. Radiopharm.*, 42, 1999, 227.

Anton Probst, et al., *Thermolysis and UV Photolysis of Perfluorinated Iodo-alkanes and Iodo-oxaalkanes: There is a Preferred Reaction Channel*; Journal of Fluorine Chemistry, 47 (1990), 163-173.

Ieva L. Reich, et al., *Synthesis of $^{14}$C-labeled Perfluorooctanoic and Perfluorodecanoic acids: Purification of Perfluorodecanoic Acid, Journal of Labelled Compounds and Radiopharmaceuticals*, 1987, vol. XXIV, No. 10.

* cited by examiner

*Primary Examiner*—Peter G O'Sullivan
*Assistant Examiner*—Sudhakar Katakam
(74) *Attorney, Agent, or Firm*—Nancy S. Mayer

(57)    ABSTRACT

Various $^{13}$C and $^{14}$C carbon labeled compounds $R_f$—$^b$CF(U)$_y$(T)$_z$    Formula 1A or $R_f$—$^b$CF$_2$$^b$CF(U)$_y$(T)$_z$    Formula 1B wherein $R_f$ is a linear or branched perfluoroalkyl radical $Z(C_mF_{2m})$—, m is 1, 3 to 20, or a mixture thereof;

Z is F when m is 1, and Z is F, Cl, or H when m is 3 to 20 or a mixture thereof;

b is 13 or 14;

y is 1, and z is 0 or 1; and when y and z are each 1, U is F, and T is selected from the group consisting of monovalent radicals —X wherein X is I or Br, —CH$_2$—CH$_2$—X, —CH=CH$_2$, —CH$_2$—CH$_2$—OH, —CH$_2$—COOH, —CH$_2$OH, —$^b$CH$_2$OH, —COOH, —$^b$COOH, —O—CF(CF$_3$)—C(O)F, —O—CF(CF$_3$)—X, —SO$_2$Y wherein Y is H, F or Cl, and —SO$_3$H; and when y is 1, and z is 0, U is selected from the group consisting of divalent radicals =CH—COOH, =CH—CH$_2$—OH, and =O, are disclosed, and a process for their preparation which selectively introduces $^{13}$C and $^{14}$C carbon labels into a fluoroalkyl chain.

2 Claims, No Drawings

SYNTHESIS OF CARBON-LABELED PERFLUOROALKYL COMPOUNDS

BACKGROUND OF THE INVENTION

There is an interest in determining the environmental and biological fate of various perfluoroalkyl compounds, including their partial decomposition products. There is as well a need for carbon labeling, which enables distinctive analytical monitoring for studying reaction kinetics and mechanisms. Perfluoroalkyl iodides ($C_nF_{(2n+1)}$—I) are important reactive intermediates in the chemistry of perfluoroalkyl compounds. The most widely used commercial route to prepare them consists of the telomerization of tetrafluoroethylene. This reaction generates the family of perfluoroalkyl iodides $C_{2n}F_{(4n+1)}$—I having an even number of carbon atoms, thus making them easily available for general synthetic use and further functionalization. For the studies described, $^{13}$C- and $^{14}$C-carbon labeled (or enriched) perfluoroalkyl or partially fluorinated alkyl derivatives are needed, wherein the labeled carbon atom is in the perfluoroalkyl group instead of within the hydrocarbon portion of the molecule. Having the labeled carbon in the perfluoroalkyl group would be advantageous because a perfluoroalkyl chain is chemically inert, and thus the carbon label would still remain a part of the partially fluorinated molecule even with the molecule's partial decomposition or conversion to other intermediates. Additionally, this stability would allow easy molecular recognition and detection in complex reaction mixtures or biological media.

Hereinafter the term "labeled" as applied to a carbon atom means that the concentration of $^{13}$C or $^{14}$C isotopic content has been significantly enriched. Commercial sources of labeled materials, such as barium carbonate-$^{13}$C, are available with a 98 percent $^{13}$C atom enrichment. Among the $^{14}$C sources, barium carbonate-$^{14}$C with higher than 50% (31.3 mCi/mmol) enrichment for $^{14}$C atom is used. The $^{14}$C isotope is radioactive, undergoing beta-decay with half-life of about 5700 years. Carbon-labeled compounds can be blended into the corresponding unlabelled ($^{12}$C) compound for studies or analytical detection, a procedure known as "spiking". Thus, the compounds with high (50-99%) isotope concentrations are preferred.

However, the synthesis of specifically labeled $^{13}$C- and $^{14}$C-carbon perfluoroalkyl compounds presents many challenges. Common fluorinated building blocks such as tetrafluoroethylene are not available in carbon-labeled form. Carbon-labeled tetrafluoroethylene is also not viewed as practical for the synthesis of individual n-perfluoroalkyl labeled materials, since it requires special safety handling measures not easily attainable in the laboratory. It is prone to polymerization, and its telomerization would lead to the mixture of homologs $X(CF_2CF_2)_nY$ rather than a single molecule. There are also considerable laboratory limitations to achieve perfluorination with powerful fluorination agents, such as elemental fluorine $F_2$, and electrochemical fluorination in liquid HF. These procedures are typically used on the industrial scale to make various perfluoroalkyl building blocks and their derivatives. It is desirable to perform such labeled syntheses primarily on the laboratory scale using ordinary laboratory equipment. The synthesis of such carbon-labeled target organic molecules primarily employs labeled carbon sources (such as $^{13\ or\ 14}CO_2$, and $Na^{13\ or\ 14}CN$) that are widely commercially available, or labeled hydrocarbon intermediates (ethylene, acetic acid, etc.) that are more expensive and limited in availability.

A possible synthetic route for the preparation of $^{13}$C- and $^{14}$C-labeled perfluoroalkyl iodides is the Hunsdieker reaction of $C_nF_{(2n+1)}$—COOAg salts with iodine. An example of such methodology is the preparation of 1-$^{14}$C-1-iodoperfluoropropane [Seleznev, V. G.; Skorobogatov, G. A., Slezar, O. N. "Photolysis of 1-$^{14}$C-perfluoropropyl iodide with powerful light pulses" *J. Org. Chem. USSR* (Eng. Transl.), 12, 1976, 259]. However, such an approach requires the multi-stage synthesis of the labeled hydrocarbon acid precursors, which are further perfluorinated. It requires electrochemical fluorination expertise, special equipment, and handling of liquid hydrogen fluoride, all of which present safety issues. Additionally, perfluorination of relatively long n-alkyl chain hydrocarbon derivatives, using electrochemical fluorination or other means, can be incomplete or be accompanied by isomerization of the labeled alkyl chain. Such mixtures would not be acceptable for the end use, and pure compounds and their isomers would be very difficult to separate.

For the environmental, biological, analytical and other programs described above, it is desirable to have an easy and safe method to selectively prepare $^{13}$C- and $^{14}$C-labeled perfluoroalkyl iodides and their derivatives wherein the labeled carbon is within the perfluoroalkyl chain.

The present invention provides a selective process for the preparation of such perfluoroalkyl iodides and derivatives having a labeled carbon atom in a specific and terminal location of the perfluoroalkyl group. The process provides access to defined labeled compounds instead of a mixture of isomers.

SUMMARY OF THE INVENTION

The present invention comprises a compound of $$R_f\!\!-\!\!^bCF(U)_y(T)_z \qquad \text{Formula 1A or}$$

$$R_f\!\!-\!\!^bCF_2{}^bCF(U)_y(T)_z \qquad \text{Formula 1B}$$

wherein $R_f$ is a linear or branched perfluoroalkyl radical $Z(C_mF_{2m})\!\!-\!\!$, m is 1, 3 to 20, or a mixture thereof;

Z is F when m is 1, and Z is F, Cl, or H when m is 3 to 20 or a mixture thereof;

b is 13 or 14;

y is 1, and z is 0 or 1; and when y and z are each 1, U is F, and T is selected from the group consisting of monovalent radicals —X wherein X is I or Br, —CH$_2$—CH$_2$—X, —CH=CH$_2$, —CH$_2$—CH$_2$—OH, —CH$_2$—COOH, —CH$_2$OH, —$^b$CH$_2$OH, —COOH, —$^b$COOH, —O—CF(CF$_3$)—C(O)F, —O—CF(CF$_3$)—X, —SO$_2$Y wherein Y is H, F or Cl, and —SO$_3$H; and when y is 1, and z is 0, U is selected from the group consisting of divalent radicals =CH—COOH, =CH—CH$_2$—OH, and =O.

The present invention further comprises a process for the preparation of a compound of $$R_f\!\!-\!\!^aCF(U)_y(T)_z \qquad \text{Formula 1C}$$

wherein $R_f$ is a linear or branched perfluoroalkyl radical $Z(C_mF_{2m})\!\!-\!\!$, m is 1, 3 to 20, or a mixture thereof;

Z is F when m is 1 and Z is selected from F, Cl, or H when m is 3 to 20 or a mixture thereof;

a is 12, 13 or 14;

y and z are each 1;

U is F; and

T is —X wherein X is I or Br, comprising
  a) contacting a perfluoroalkyl metallic compound with $^aCO_2$ to generate the corresponding acid;
  b) contacting the acid from step a) with a fluorinating agent to yield $R_f\text{—}^aC(O)F$;
  c) contacting the $R_f\text{—}^aC(O)F$ with a substituted trifluorooxirane in the presence of a fluoride ion source to yield $R_f\text{—}^aCF_2\text{—}O\text{—}CF[(CF_2)_pR'']\text{—}C(O)F$ wherein R" is H or F and p is 1 to 8; and
  d) contacting $R_f\text{—}^aCF_2\text{—}O\text{—}CF[(CF_2)_pR'']\text{—}C(O)F$ with a metal iodide or metal bromide and heating to yield $R_f\text{—}^aCF(U)_y(T)_z$.

The present invention further comprises a process for the preparation of a compound of $$R_f\text{—}^bCF_2{}^bCF(U)_y(T)_z \qquad \text{Formula 1B}$$

wherein $R_f$ is a linear or branched perfluoroalkyl radical $Z(C_mF_{2m})$—, m is 1, 3 to 20, or a mixture thereof;

Z is F when m is 1 and Z is selected from F, Cl, or H when m is 3 to 20 or a mixture thereof;

b is 13 or 14;

y and z are each 1;

U is F; and

T is —X wherein X is I or Br, comprising
  a) contacting a perfluoroalkyl metallic compound of formula $$(R_f)_{(v-w)}{}^bCF_2MX_w$$

wherein $R_f$ is a linear or branched perfluoroalkyl radical $Z(C_mF_{2m})$—,

M is selected from the group consisting of Zn, Li, Cd, Mg, Ca, and amalgams thereof with Hg, X is I or Br, v is the valence of M, w is 0 or 1, and b is 13 or 14, with $^bCO_2$ to generate the corresponding acid;

b) contacting the acid from step a) with a fluorinating agent to yield $R_f\text{—}^bCF_2{}^bC(O)F$;
  c) contacting the $R_f\text{—}^bCF_2{}^bC(O)F$ with a substituted trifluorooxirane in the presence of a fluoride ion source to yield $R_f\text{—}^aCF_2\text{—}O\text{—}CF[(CF_2)_pR'']\text{—}C(O)F$ wherein R" is H or F and p is 1 to 8; and
  d) contacting $R_f\text{—}^aCF_2\text{—}O\text{—}CF[(CF_2)_pR'']\text{—}C(O)F$ with a metal iodide or metal bromide and heating to yield $R_f\text{—}^bCF_2{}^bCF(U)_y(T)_z$.

The present invention further comprises a process for the preparation of a compound of formula $$R_f\text{—}^bCF_2\text{—}^bCOOH$$

wherein $R_f$ is a linear or branched perfluoroalkyl radical $Z(C_mF_{2m})$—, Z is F, and m is 3 to 20 or a mixture thereof, comprising contacting $R_f\text{—}^bCF_2X$ wherein $R_f$ is as defined above and X is Br or I with an organometallic compound R—Mg—X or R—Li wherein R is a $C_1$-$C_4$ alkyl and X is Br or I, and $^bCO_2$ to generate $R_f\text{—}^bCH_2\text{—}^bCOOH$.

DETAILED DESCRIPTION

Trademarks are shown in upper case.

The term "labeled" as used herein is applied to a carbon atom where the concentration or isotopic content of $^{13}C$ or $^{14}C$ has been significantly enriched. The range of necessary enrichment differs for $^{13}C$ and $^{14}C$ enrichment since $^{13}C$, in contrast to $^{14}C$, occurs significantly in the natural environment, to the extent of about 1.1%. Thus for $^{13}C$ labeling, the proportion of $^{13}C$ at a specific atom location is at least about 50%, preferably at least about 90%, and most preferably at least 98%. For $^{14}C$ labeling, the proportion of $^{14}C$ at a specific atom location is at least about 10%, preferably at least about 25%, and most preferably at least 50%, with high radiochemical purity. The present invention provides isotopically labeled $^{13}C$- or $^{14}C$-labeled fluorinated compounds wherein a labeled carbon is within the perfluoroalkyl chain, and compounds having two or more labeled carbons present. The present invention further provides synthetic routes to make the desired labeled compounds maintaining the $^{14}C/^{12}C$ or $^{13}C/^{12}C$ isotope ratio equal or similar to the starting carbon-labeled material. The synthetic routes of the present invention also provide a process for extending the perfluoroalkyl chain of perfluoroalkyl halides $C_nF_{(2n+1)}X$ wherein X is Br or I using stepwise fluorination of a terminal carboxy group of perfluoroalkyl carboxylic acids $C_nF_{(2n+1)}\text{—}COOH$, yielding the useful $C_nF_{(2n+1)}CF_2X$ halides. This extension of the perfluoroalkyl chain is useful with both labeled and unlabeled compounds.

This invention comprises isotopically $^{13}C$— or $^{14}C$-labeled fluorinated compounds with linear and branched perfluoroalkyl chains of the structure of Formula 1A or Formula 1B, and derivatives thereof;

$$R_f\text{—}^bCF(U)_y(T)_z \qquad \text{Formula 1A}$$

$$R_f\text{—}^bCF_2{}^bCF(U)_y(T)_2 \qquad \text{Formula 1B}$$

wherein $R_f$ is a linear or branched perfluoroalkyl radical $Z(C_mF_{2m})$—, wherein m is 1, 3 to 20, or a mixture thereof; Z is F when m is 1 and Z is selected from F, Cl, or H when m is 3 to 20 or a mixture thereof; b is 13 or 14; y is 1, and z is 0 or 1; and when y and z are each 1, U is F, and T is selected from the group consisting of monovalent radicals —X, wherein X is I or Br; —$CH_2$—$CH_2$—X; —CH=$CH_2$; —$CH_2$—$CH_2$—OH; —$CH_2$—COOH; —$CH_2$—OH; —$^bCH_2$—OH; —COOH; —$^b$COOH; —O—CF($CF_3$)—C(O)F; —O—CF($CF_3$)—X; —$SO_2Y$, wherein Y is H, F, or Cl; and —$SO_3H$; and when y is 1 and z is 0, U is selected from the group consisting of divalent radicals =CH—COOH, =CH—$CH_2$—OH, and =O.

Specific examples of Formula 1A are $R_f\text{—}^bCF_2$—X, $R^f\text{—}^bCF_2\text{—}CH_2CH_2X$, $R_f\text{—}^bCF_2$—CH=$CH_2$, $R_f\text{—}^bCF_2$—$CH_2$—$CH_2$—OH, $R^f\text{—}^bCF_2$—$CH_2$—COOH, $R_f\text{—}^bCF_2$—$CH_2OH$, $R_f\text{—}^bCF_2$—COOH, $R_f\text{—}^bCF_2{}^b$COOH, $R_f\text{—}^bCF_2$—OCF($CF_3$)—C(O)F, $R_f\text{—}^bCF_2$—OCF($CF_3$)—I, $R_f\text{—}^bCF_2$—$SO_2$—H, $R_f\text{—}^bCF_2$—$SO_2$—Cl, $R_f\text{—}^bCF_2$—$SO_2$—F, $R_f\text{—}^bCF_2$—$SO_3$—H, $R_f\text{—}^bCF$=CH—COOH, $R_f\text{—}^bCF$=CH—$CH_2$—OH, and $R_f\text{—}^bCOF$.

Specific examples of Formula 1B are $R_f\text{—}^bCF_2{}^bCF_2X$, $R_f\text{—}^bCF_2{}^bCF_2$—$CH_2CH_2X$, $R_f\text{—}^bCF_2{}^bCF_2$—CH=$CH_2$, $R_f\text{—}^bCF_2{}^bCF_2$—$CH_2$—$CH_2$—OH, $R_f\text{—}^bCF_2{}^bCF_2$—$CH_2$—COOH, $R_f\text{—}^bCF_2{}^bCF_2$—$CH_2OH$, $R_f\text{—}^bCF_2{}^bCF_2$—COOH, $R_f\text{—}^bCF_2{}^bCF_2{}^b$COOH, $R_f\text{—}^bCF_2{}^bCF_2$—OCF($CF_3$)—C(O)F, $R_f\text{—}^bCF_2{}^bCF_2$—OCF($CF_3$)—I, $R_f\text{—}^bCF_2{}^bCF_2$—$SO_2$—H, $R_f\text{—}^bCF_2{}^bCF_2$—$SO_2$—Cl, $R_f\text{—}^bCF_2{}^bCF_2$—$SO_2$—F, $R_f$—$^bCF_2^bCF_2$—$SO_3$—H,  $R_f$—$^bCF_2^bCF$=CH—COOH $R_f$—$^bCF_2^bCF$=CH—$CH_2$—OH, and $R_f$—$^bCOF$.

Of particular interest are the above compounds wherein for $R_f$ equal to $Z(C_mF_{2m})$—, m is a positive integer of from 4 to 14, preferably wherein m is 6, 7, 8 and 9 and mixtures thereof. Preferred for their utility in making various derivative compounds are $C_6F_{13}{}^bCF_2$—I, $C_6F_{13}{}^bCF_2$—COOH, $C_6F_{13}$—$^bCF_2$—$^bCOOH$, $C_7F_{15}$—$^bCF_2$—I, $C_7F_{15}{}^bCF_2$—$SO_2Cl$, and $C_7F_{15}{}^bCF_2\,CH_2CH_2OH$ wherein b is 13 or 14.

The present invention also comprises processes for the preparation of said compounds. The processes of the present invention can also be used to prepare the corresponding unlabeled $^{12}C$-compounds.

The processes of the present invention provide convenient synthetic methods to selectively introduce $^{13}C$ and $^{14}C$-carbon labels into a terminal position of the fluoroalkyl chain. If desired, the conversion sequence of $R_f$—X wherein X is I or Br into $R_f$—$^aCF_2$—X (wherein X is I or Br and a is 12, 13, or 14) is repeated to prepare the longer chain homologues $C_nF_{(2n+1)}{}^aCF_2{}^aCF_2X$ with two added $CF_2$ groups that are labeled or unlabelled, i.e., with an additional $^{12}CF_2$, $^{13}CF_2$, or $^{14}CF_2$ carbon atom in the fluoroalkyl chain. The doubly labeled $^{13}C$ analogs where the $C_nF_{(2n+1)}{}^{13}CF_2{}^{13}CF_2X$ materials have a molecular weight greater by two units than the corresponding unlabeled ($^{12}C$) parent compounds are especially useful for unambiguous mass-specific recognition.

The processes of the invention do not use perfluorination with elemental fluorine or electrochemical fluorination, thus the synthesis can be accomplished by using ordinary laboratory equipment and glassware.

The processes of the present invention comprise a synthetic pathway that utilizes the synthesis of substituted trifluorooxirane based intermediates, preferably hexafluoropropylene oxide based intermediates. It achieves the fluorination to introduce two fluorine atoms in stepwise fashion using low reaction temperatures and mild reaction conditions. The final thermolysis yields the desired $R_f$—$^aCF_2$—X or $R_f$—$^bCF_2{}^bCF_2X$ materials wherein X is Br or I and elimination of CO and $CF_3C(O)F$. Various derivatives are prepared from the carbon labeled perfluoroalkyl halide using known reactions, thus yielding a broad array of carbon labeled compounds.

In summary, a process is provided for the preparation of a compound of $R_f$—$^aCF(U)_y(T)_z$  Formula 1C wherein $R_f$ is a linear or branched perfluoroalkyl radical $Z(C_mF_{2m})$—, m is 1, 3 to 20, or a mixture thereof;

Z is F when m is 1 and Z is selected from F, Cl, or H when m is 3 to 20 or a mixture thereof;

a is 12, 13 or 14;

y and z are each 1;

U is F; and

T is —X wherein X is I or Br, comprising
  a) contacting a perfluoroalkyl metallic compound with $^aCO_2$ to generate the corresponding acid;
  b) contacting the acid from step a) with a fluorinating agent to yield $R_f$—$^aC(O)F$;
  c) contacting the $R_f$—$^aC(O)F$ with a substituted trifluorooxirane in the presence of a fluoride ion source to yield $R_f$—$^aCF_2$—O—$CF[(CF_2)_pR'']$—$C(O)F$ wherein R" is H or F and p is 1 to 8; and
  d) contacting $R_f$—$^aCF_2O$—$CF[(CF_2)_pR]$—$C(O)F$ with a metal iodide or metal bromide and heating to yield $R_f$—$^aCF(U)_y(T)_z$.

A further process is provided for the preparation of a compound of formula 1B $R_f$—$^bCF_2{}^bCF_2CF(U)_y(T)_z$ wherein $R_f$, U, T, y and z are as defined above and b is 13 or 14, comprising
  a) contacting a perfluoroalkyl metallic compound of formula $(R_f)_{(v-w)}{}^bCF_2MX_w$ wherein $R_f$ is a linear or branched perfluoroalkyl radical $Z(C_mF_{2m})$—, M is selected from the group consisting of Zn, Li, Cd, Mg, Ca, and amalgams thereof with Hg, X is I or Br, v is the valence of M, w is 0 or 1, and b is 13 or 14, with $CO_2$ to generate the corresponding acid;
  b) contacting the acid from step a) with a fluorinating agent to yield $R_f$—$^bCF_2{}^bC(O)F$;
  c) contacting the $R_f$—$^bCF_2{}^bC(O)F$ with a substituted trifluorooxirane in the presence of a fluoride ion source to yield $R_f$—$^aCF_2$—O—$CF[(CF_2)_pR'']$—$C(O)F$ wherein R" is H or F and p is 1 to 8; and
  d) contacting $R_f$—$^aCF_2$—O—$CF[(CF_2)_pR'']$—$C(O)F$ with a metal iodide or metal bromide and heating to yield $R_f$—$^bCF_2{}^bCF(U)_y(T)_z$.

For clarity, each stage of the synthetic process is described below with generic formulae and followed by a specific example for the preparation of compounds of Formula 1C. Analogous steps are employed for the preparation of compounds of Formula 1B using the corresponding labeled halide as a starting material.

Perfluoroalkyl metallic compounds of the formula $(R_f)_{(v-w)}MX_w$ or $(R_f)_{(v-w)}{}^bCF_2MX_w$ wherein M is selected from the metals Ca, Li, Cd, Mg, or Zn, or amalgams thereof with mercury, v is the valency of metal M, w is 0 or 1, and $R_f$ and X are as defined above, are prepared from $R_f$—X or $R_f$—$^bCF_2$—X respectively by convenient halogen-metal exchange reactions with organometallic reagents, by trans-metallation (metal exchange) reactions, or by direct reaction of $R_f$—X or $R_f$—$^bCF_2$—X with metals. Such organometallic reagents include for example, methyl lithium of formula R—Li, or alkyl or aryl Grignard reagents of the formula R—Mg—X wherein R is an aryl or short chain alkyl group such as $C_1$-$C_4$ alkyl, preferably ethyl, selected for easy removal of the byproduct R—X. In the direct reaction of $R_f$—X or $R_f$—$^bCF_2$—X with metal, suitable metals include zinc, magnesium, calcium, cadmium, and the like. This reaction is conducted in a suitable solvent, such as diethyl ether, tetrahydrofuran, dioxane, dimethylformamide, dimethylsulfoxide, or their combinations, which selection is dependent on the nature of $(R_f)_{(v-w)}MX_w$ or $(R_f)_{(v-w)}{}^bCF_2MX_w$. These perfluoroalkyl metallic compounds are contacted with $^aCO_2$ or $^bCO_2$, which is added sequentially or is present throughout the course of the preparation of $(R_f)_{(v-w)}MX_w$ or $(R_f)_{(v-w)}{}^bCF_2MX_w$ to give, after hydrolysis, labeled acids $R_f$—$^a$COOH or $R_f$—$^b$CF$_2$$^b$COOH. $^a$CO$_2$ or $^b$CO$_2$ is prepared from commercially available sources, such as Ba$^{13}$CO$_3$ or Ba$^{14}$CO$_3$. $^{13}$CO$_2$ is preferably prepared from Ba$^{13}$CO$_3$ by controlled addition of concentrated sulfuric acid. In a specific example, ethyl magnesium bromide is selected for easy removal of the byproduct ethyl iodide after the reaction, and to obtain satisfactory high yield of the desired product:

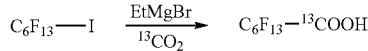

At from about −30° C. to about 20° C., $R_f$—$^a$COOH or $R_f$—$^b$CF$_2$$^b$COOH is most conveniently converted in high yield to the acid fluoride $R_f$—$^a$C(O)F or $R_f$—$^b$CF$_2$$^b$C(O)F respectively in one step by its contact with a fluorinating agent. Commercially available liquid fluorinating agents like N,N-diethylaminosulfur trifluoride (DAST) or DEOXO-FLUOR™ [bis(2-methoxyethyl)aminosulfur trifluoride] are preferable for use in the laboratory for this conversion over the gaseous and toxic sulfur tetrafluoride SF$_4$. The fluorinating agent can alternatively be N,N-dialkylaminotrifluorosulfurane, cyclohexylaminotrifluorosulfurane, cyclopentylaminotrifluorosulfurane, alkylphenylaminotrifluorosulfurane, or morpholinotrifluorosulfurane. The product obtained has a low boiling point and is easily isolated from the reaction medium by vacuum transfer. HF is generated and trapped during the vacuum transfer into a suitable trap such as a liquid nitrogen trap. In a variation of this method the acid $R_f$—$^a$COOH or $R_f$—$^b$CF$_2$$^b$COOH is converted into acid chloride $R_f$—$^a$C(O)Cl or $R_f$—$^b$CF$_2$$^b$C(O)Cl respectively, by the reaction with inexpensive laboratory chlorinating reagents, such as SOCl$_2$, which is then converted into the $R_f$—$^a$C(O)F or $R_f$—$^b$CF$_2$$^b$C(O)F in a halogen exchange reaction by contacting the above N,N-diaklyaminotrifluorosulfuranes or other anhydrous inorganic fluorides, such as KF, NaF, SbF$_3$, with the acid chloride, where complete conversion is desirable. A specific example of this reaction is:

The $R_f$—$^a$C(O)F or $R_f$—$^b$CF$_2$$^b$C(O)F is then contacted with a substituted trifluorooxirane in the presence of a fluoride ion source to yield $R_f$—$^a$CF$_2$—O—CF[(CF$_2$)$_p$R]—C(O)F or $R_f$—$^b$CF$_2$b CF$_2$—O—CF[(CF$_2$)$_p$R"]—C(O)F, wherein R" is H or F and p is 1 to 8. Suitable substituted trifluorooxiranes include perfluoroalkyltrifluorooxirane or omega H-perfluoroalkyltrifluorooxirane. Examples include H(CF$_2$)$_p$-c-CFCF$_2$O, and F(CF$_2$)$_p$-c-CFCF$_2$O, wherein p is 1 to 8. Preferred is an n-perfluoroalkyl-1-ene oxide, such as commercially available hexafluoropropylene oxide. An example fluoride ion source is potassium fluoride. Selection of a suitable anhydrous solvent and a fluoride ion source aids in achieving the addition of only one hexafluoropropylene unit with high selectivity and high conversion. Suitable solvents include acetonitrile and glymes such as tetra(ethylene glycol) dimethyl ether (tetraglyme). A specific example of this reaction is:

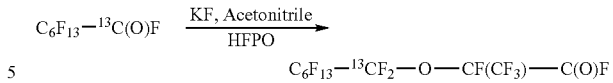

The resultant $R_f$—$^a$CF$_2$—O—CF[(CF$_2$)$_p$R"]—C(O)F or $R_f$—$^b$CF$_2$—$^b$CF$_2$—O—CF[(CF$_2$)$_p$R"]—C(O)F is contacted with metal iodide or metal bromide to form acid iodide or acid bromide respectively, and decarbonylated upon heating to yield $R_f$—$^a$CF$_2$—O—CF(CF$_3$)—X or $R_f$—$^b$CF$_2$$^b$CF$_2$—O—CF(CF$_3$)—X, wherein X is iodide or bromide, with the elimination of carbon monoxide. The most preferable metal iodide is lithium iodide. A specific example of this reaction is:

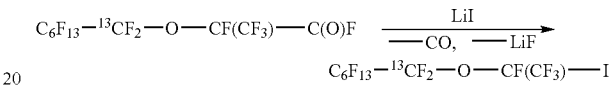

The $R_f$—$^a$CF$_2$—O—CF(CF$_3$)—X or $R_f$—$^b$CF$_2$$^b$CF$_2$—O—CF(CF$_3$)—X is heated above 210° C. to yield $R_f$—$^a$CF$_2$—X or $R_f$—$^b$CF$_2$$^b$CF$_2$—X respectively. A specific example is:

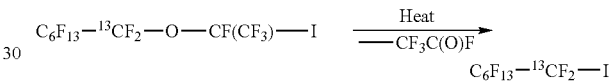

Further details of the experimental procedures are shown in the Examples.

The process of the present invention further comprises the conversion of, for instance, $C_nF_{(2n+1)}$X into $C_nF_{(2n+1)}$—$^a$CF$_2$X, wherein X is iodide or bromide, using hexafluoropropylene oxide in synthetic methods that make available intermediate acid fluorides and secondary iodides or bromides of substituted perfluoroalkyl ethers.

The process of the present invention is used to prepare various terminal perfluoroalkyl iodides $C_nF_{(2n+1)}$—$^a$CF$_2$I or bromides $C_nF_{(2n+1)}$—$^a$CF$_2$Br starting from $C_nF_{(2n+1)}$—X wherein X is Br or I. Examples of 1-$^{13}$C— (or $^{14}$C—) labeled 1-iodoperfluoroalkane include 1-$^{13}$C-1-iodoperfluorooctane, 1-$^{13}$C-1-iodoperfluoroheptane, and 1-$^{14}$C-1-iodoperfluorooctane. These carbon-labeled 1-iodoperfluoroalkanes are functionalized to make a variety of labeled perfluoroalkyl derivatives including 1,2-di-$^{13}$C-perfluorooctanoic acid (by the carboxylation of $C_6F_{13}$—$^{13}$CF$_2$—I with $^{13}$CO$_2$), 1-iodo-1H,1H,2H,2H-3-$^{13}$C (or 1-$^{14}$C)-perfluorodecane (by the addition of ethylene to $C_7F_{15}$—$^{13(or\ 14)}$CF$_2$—I), and 1H,1H, 2H,2H-3-$^{13}$C (or $^{14}$C)-perfluorodecan-1-ol (by hydrolysis of $C_7F_{15}$—$^{13(or\ 14)}$CF$_2$—CH$_2$CH$_2$I) using known synthetic methods.

The above-described process of the present invention is also used to extend the perfluoroalkyl chain in $C_nF_{(2n+1)}$—I or $C_nF_{(2n+1)}$Br with CF$_2$ groups. If used in part the method can be applied to introduce the —CF$_2$I group or —CF$_2$Br and to prepare perfluoroalkyl halides $C_nF_{(2n+1)}$—$^a$CF$_2$X (n=3 to 20) and their derivatives starting from other reactive intermediates such as fluorinated carboxylic acids $C_nF_{(2n+1)}$—$^a$COOH, or acid fluorides $C_nF_{(2n+1)}$—$^a$C(O)F. Such carboxylic acids and acid fluorides are prepared by various methods, and then subjected to subsequent addition of one substituted trifluorooxirane unit, such as a hexafluoropropylene oxide (HFPO)

unit, to such acid fluorides to obtain HFPO adducts $C_nF_{(2n+1)}$—$^aCF_2OCF(CF_3)C(O)F$, and sequential further reactions with lithium halide to obtain secondary halides $C_nF_{(2n+1)}$—$^aCF_2OCF(CF_3)X$, and then thermal decomposition to make primary halides $C_nF_{(2n+1)}$—$^aCF_2X$.

The labeled perfluoroalkyl- and highly fluorinated alkyl halides of the present invention are derivatized by various synthetic methods that have been conventionally applied to the corresponding unlabeled halides, yielding derivatives containing labeled carbon in the terminal position of the fluoroalkyl chain. A particularly useful family of products is derived from the adduct of the perfluoroalkyl iodide and ethylene to yield the 1H, 1H,2H,2H-perfluoroalkyl iodide, $F(C_mF_{2m})_n{}^bCF_2CH_2CH_2I$. 1H,1H,2H,2H-perfluoroalkyl iodide is hydrolyzed to the corresponding 1H,1H,2H,2H-perfluoroalkanol, $F(C_mF_{2m})_n{}^bCF_2CH_2CH_2OH$, from which (meth)acrylate monomers and then fluorinated (meth)acrylate polymers are prepared. Reaction of the 1H,1H,2H,2H-perfluoroalkan-1-ol with polyisocyanates yields fluorinated polyurethane polymers. Dehydrohalogenation of 1H,1H,2H,2H-perfluoroalkyl iodide yields the terminal olefin 1H,1H,2H-perfluoroalkene, $F(C_mF_{2m})_n{}^bCF_2CH=CH_2$. Dehydrofluorination of 1H,1H,2H,2H-perfluoroalkan-1-ol with strong bases leads to the formation of unsaturated alcohol $F(C_mF_{2m})_n{}^bCF=CHCH_2OH$. Oxidation of 1H,1H,2H,2H-perfluoroalkan-1-ol yields the 2H,2H-perfluoroalkanoic acid $F(C_mF_{2m})_n{}^bCF_2CH_2COOH$. Dehydrofluorination of the 2H,2H-perfluoroalkanoic acid yields the unsaturated acid $F(C_mF_{2m})_n{}^bCF=CHCOOH$. $F(C_mF_{2m})_n{}^bCF_2I$ subjected to deiodosulfination with sodium dithionite $Na_2S_2O_4$ yields perfluoroalkyl sulfinic acid $F(C_mF_{2m})_n{}^bCF_2SO_2H$. Perfluoroalkyl sulfinic acid $F(C_mF_{2m})_n{}^bCF_2SO_2H$ can be further chlorinated with chlorine $Cl_2$ to form sulfonyl chloride $F(C_mF_{2m})_n{}^bCF_2SO_2Cl$. The above sulfonyl chloride $F(C_mF_{2m})_n{}^bCF_2SO_2Cl$ is used to prepare sulfonyl fluoride $F(C_mF_{2m})_n{}^bCF_2SO_2F$ by the reaction with laboratory fluorinating agents such as DAST or metal fluorides such as KF, and converted to functional sulfonamides and their alcohol derivatives $F(C_mF_{2m})_n{}^bCF_2SO_2NR'CH_2CH_2OH$, wherein R' is a short chain alkyl which are used to prepare polyurethane and (meth)acrylate polymers.

Thus, the labeled compounds of the present invention are readily derivatized into a wide range of the labeled perfluoroalkyl compounds. The $^{12}C$-analogs of these compounds are important commercial intermediates and products.

The present invention also includes a process for the preparation of a compound of formula $$R_f\text{—}^bCF_2\text{—}^bCOOH$$

wherein $R_f$ is a linear or branched perfluoroalkyl radical $Z(C_mF_{2m})$—, Z is F, and m is 3 to 20 or a mixture thereof, comprising contacting $R_f$—$^bCF_2X$ wherein $R_f$ is as defined above and X is Br or I with an organometallic compound R—Mg—X or R—Li wherein R is a $C_1$-$C_4$ alkyl and X is Br or I, and $^bCO_2$ to generate $R_f$—$^bCH_2$—$^bCOOH$.

The iodide obtained from the process of the present invention is used to prepare several derivative compounds. For instance, the perfluoroalkyl metallic reagent, which is prepared from the labeled $R_f$—$^bCF_2$—X by the convenient metal exchange reactions including alkyl (or aryl) Grignard reagents, or a direct reaction of with metals (such as zinc), is contacted with $^bCO_2$, which is added sequentially or is present throughout the course of the reaction, to give, after hydrolysis, double di-1,2-$^bC$-labeled acids $R_f$—$^bCF_2$—$^bCOOH$, or, in case of using $^{12}CO_2$, obtaining 2-$^bC$-labeled acids $R_f$—$^bCF_2$—COOH with the carbon labeled atom as a part of perfluoroalkyl chain. A specific doubly labeled example is:

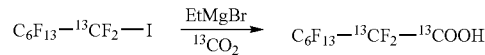

The singly labeled $R_f$—$^bCF_2$—COOH or the doubly labeled $R_f$—$^bCF_2$—$^bCOOH$ perfluoroalkyl chain acids, available by the above reaction, are further reduced by lithium aluminum hydride or by hydrogen in the presence of a catalyst to the corresponding singly labeled $R_f$—$^bCF_2$—$CH_2OH$ or doubly labeled alcohols $R_f$—$^bCF_2$—$^bCH_2OH$.

The carbon labeled compounds of the present invention are useful because such carbon labeled materials, including heavier molecular weight M+n, (n=1-5) standards, can be easily detected by mass selective spectroscopy and nuclear magnetic resonance NMR. $^{13}C$, $^1H$ NMR, and other isotope specific analyses, as well as radioactive detection of $^{14}C$-isotope labeled molecules can detect such compounds in various reaction mixtures and biological systems. Therefore, these carbon-labeled materials are useful for a wide variety of studies including chemical and physicochemical (to determine the reactants and their products in complex chemical mixtures), kinetic studies, toxicological (pharmacokinetics, microsome and hepatocyte metabolism) environmental fate (biodegradation under aerobic and anaerobic conditions) and others. The processes of the present invention are useful to prepare various carbon-labeled compounds or to selectively introduce labeled carbons at desired positions.

Materials

1. Ethyl Magnesium bromide, acetonitrile, anhydrous potassium fluoride, and DEOXO-FLUOR (bis(2-methoxyethyl)aminosulfur trifluoride) are available from Aldrich, Milwaukee Wis.

2. n-$C_6F_{13}$—I and hexafluoropropylene oxide (HFPO) is available from Lancaster, Windham, N.H.

3. DAST (N,N-Diethylamino sulfur trifluoride) is available from Aldrich, Milwaukee Wis. or SynQuest Laboratories, Inc., Alachua, Fla.

4. VERTREL-XF (2H,3H-Perfluoropentane) is available from Oakwood Products, Inc. (Fluorochem USA) West Columbia, S.C.

5. $Ba^{13}CO_3$ (98% $^{13}C$) and $CD_2=CD_2$ is available from ISOTEC, Inc. Miamisburg, Ohio.

6. $Ba^{14}CO_3$ is available from SIGMA, St. Louis, Mo.

EXAMPLES

The examples provided below demonstrate the key steps of the technology, and are not intended to limit the scope of the present invention. The procedures of the examples are also applicable to unlabeled ($^{12}C$) compositions and labeled $^{14}C$ compositions.

Example 1

$C_6F_{13}$-Grignard reagent was prepared under nitrogen from commercially available $C_6F_{13}I$ (83.6 g) in anhydrous ether 1.1 L, by the addition of EtMgBr 70 mL (3M sol. in ether), at −62-70° C., reacted for 40 min, and cooled to −95° C. 375 mL of THF were added. $^{13}CO_2$, generated from $Ba^{13}CO_3$ (28.3 g) by the addition of concentrated $H_2SO_4$, was introduced into the reaction, which was gradually warmed to −70-78° C., stirred for 5-6 hours and then slowly warmed to room temperature (overnight). 10 mL of water were added and the solvent was distilled off at ambient pressure (<100° C. in the reaction vessel) following by brief application of vacuum (30 Torr, 4 kPa). Aqueous sodium hydroxide solution (5%) was added and the crude material was washed with pentane. The aqueous layer was treated with $H_2SO_4$ (to obtain a resulting 20% $H_2SO_4$ solution). The crude acid $C_6F_{13}$—$^{13}COOH$ (62.7 g) was separated as the bottom layer and further distilled in vacuum.

Conversion of $C_6F_{13}$—$^{13}COOH$ (132.4 g, prepared as described above) into acid fluoride $C_6F_{13}$—$^{13}C(O)F$ was made by slowly adding DAST (91.5 g, 1.5 eq.) at −30 to 20° C. (exotherm), followed by transfer of the product (104.2 g) in vacuum (20° C./5-10 Torr, 0.67-1.3 kPa). Caution: HF, generated during the reaction, was trapped during the vacuum transfer into the liquid nitrogen trap.

A 4-neck 250-mL flask, equipped with magnetic stirring, dry-ice cooled condenser, thermocouple, and inlet tube, was charged with 1-$^{13}C$ perfluoroheptanoic acid fluoride ($C_6F_{13}$—$^{13}C(O)F$, 103.5 g, prepared as described above), dry potassium fluoride (4.0 g), and acetonitrile (4.3 g). Hexafluoropropene oxide (HFPO, 69.5 g, 1.5 eq. overall) was slowly introduced into the flask over a period of 16 hours, maintaining the reaction temperature in the range 24-40° C. HFPO refluxed during this addition, and a 40-60° C. warm-water bath was used to maintain the temperature. The reaction provided 1:1-HFPO adduct $C_6F_{13}$—$^{13}CF_2OCF(CF_3)C(O)F$ with high selectivity and greater than 95% conversion (GC/MS). The product $C_6F_{13}$—$^{13}CF_2OCF(CF_3)C(O)F$ was transferred in vacuum to obtain 134.82 g of crude product (pot temperature 30-56° C.) at 24 Torr (3.2 kPa). A small top layer of distillate, primarily acetonitrile (7.6 g), was decanted.

1:1-HFPO adduct ($C_6F_{13}$—$^{13}CF_2OCF(CF_3)C(O)F$, 127.0 g, prepared as described above was reacted at 164-168° C. (reflux) overnight with dry lithium iodide (42.0 g) to obtain the secondary iodide $C_6F_{13}$—$^{13}CF_2OCF(CF_3)I$. A foreshot of volatile materials that distilled at the beginning of the reaction (161-172° C., b.p.=90-132° C.) was rejected. The gasses were scrubbed using aqueous sodium hydroxide. The crude product was distilled under vacuum (96.5 g, 66° C./30 Torr (4.0 kPa) to 54° C./5 Torr (0.67 kPa)). Iodine was separated at the bottom of the flask to obtain clear dark pink liquid.

Crude secondary iodide ($C_6F_{13}$$^{13}CF_2OCF(CF_3)I$, 93 g, prepared as described above) was heated at 235-240° C. for 4-6 h in a closed system. The container was cooled to 0-25° C. and carefully opened to evaporate the $CF_3C(O)F$ byproduct (scrubbing the gases using aqueous sodium hydroxide solution). 74.8 g of product $C_6F_{13}$—$^{13}CF_2I$ (a light pink liquid, overall 76.0 g) were purified by vacuum distillation on 10-plate column to obtain $C_6F_{13}$—$^{13}CF_2I$ (33.0 g 68° C./67 Torr (8.9 kPa)) with 99.1-99.7% purity, established by GC/MS.

Example 2

$C_6F_{13}$—$^{13}CF_2$—I (31.5 g) (prepared as in Example 1 above) was carboxylated with $^{13}CO_2$ (12.0 g of $Ba^{13}CO_3$) using the procedure of Example 1. The resulting crude acid $C_6F_{13}$—$^{13}CF_2$$^{13}COOH$ (22.8 g) was distilled in vacuum. A first fraction of 1.36 g was rejected. The second fraction (21.3 g, 77-83° C./3 Torr, 0.4 kPa) was further crystallized by double recrystallization from small amount of VERTREL-XF to obtain 99.5% pure $C_6F_{13}$—$^{13}CF_2$$^{13}COOH$ ($^1H$, $^{19}F$ NMR and GC/MS).

Example 3

$C_7F_{15}I$ (32.3 g) was reacted with EtMgBr (22.5 mL of 3M sol. in ether) and $^{13}CO_2$ generated from $Ba^{13}CO_3$ (10.0 g) as described in Example 1. Crude $C_7F_{15}$$^{13}COOH$ acid was crystallized from 1,1,2-trichlorotrifluoroethane to obtain 13.2 g of purified product.

$C_7F_{15}$$^{13}COOH$ (41.6 g), prepared as described above, was reacted with DEOXO-FLUOR (29.4 g) at −30 to 20° C. (exotherm). The product $C_7F_{15}$$^{13}C(O)F$ (38.4 g) was transferred in vacuum at (15-20° C./5-10 Torr).

$C_7F_{15}$$^{13}C(O)F$ (59.5 g), prepared as described above, KF (4.2 g), acetonitrile (4.8 g) was reacted with hexafluoropropylene oxide (HFPO) (67 g) over 16 hours as described in Example 1. The product $C_7F_{15}$$^{13}CF_2OCF(CF_3)C(O)F$ (72 g) was distilled in vacuum from warm water bath (60° C./1 Torr).

$C_7F_{15}$$^{13}CF_2OCF(CF_3)C(O)F$ (118.8 g), prepared as described above, was stirred and heated at 164-175° C. with lithium iodide (38.1 g) overnight. The product was distilled in vacuum to obtain 93.3 g of $C_7F_{15}$$^{13}CF_2OCF(CF_3)I$.

$C_7F_{15}$$^{13}CF_2OCF(CF_3)I$ (13.8 g) was evacuated and heated to 220-250° C. for 2.5 hours in closed 250 mL glass flask equipped with TEFLON stopper. After cooling (−10-0° C.) the flask was carefully opened and slowly warmed to evaporate the $CF_3C(O)F$ (scrubbed by aqueous sodium hydroxide solution). 11.8 g of crude product $C_6F_{13}$—$^{13}CF_2I$ were obtained, and further purified by fractional distillation in vacuum on 10 plate column to obtain $C_7F_{15}$$^{13}CF_2I$ (94° C./21 Torr, purity 98% GC/MS).

Example 4

$C_7F_{15}$-$^{13}CF_2I$ (18.5 g, 33.8 mmol) was charged into a 100-mL stainless steel autoclave, closed and evacuated. Ethylene-$d_4$ $CD_2$=$CD_2$ (small excess) was charged into the container in two portions, heated and reacted at 200° C./pressure 30-67 psi for 6.5 hours. The reaction mass was cooled, and the excess of ethylene vented off to obtain $C_7F_{15}$$^{13}CF_2CD_2$-$C_2I$ (17.0 g, 29.6 mmol, yield 87.5%), which was used for further reaction without additional purification.

Example 5

$C_8F_{17}$$^{13}CF_2CH_2CH_2I$ (16 g, 26.4 mmol) 4 mL of water and 44 g of N,N-dimethylformamide were reacted at 125° C. for 30 hours. When the conversion of $C_8F_{17}$$^{13}CF_2CH_2CH_2I$ was complete (GC), hot deionized water (28 mL) 45° C. was added. Maintaining the temperature at 40-60° C., the product was extracted with VERTREL-XF and diethyl ether, and washed with water. Solvent was removed in vacuum to obtain 14.0 g of crude material, containing 20% (GC) of $C_7F_{15}$-$^{13}CF_2$—CD=$CD_2$. It was further distilled and purified by column chromatography on silicagel (60-200 mesh) to isolate 11.0 g of $C_7F_{15}$$^{13}CF_2CD_2CD_2$-OH (96% pure, GC/FID) from the fractions enriched in $C_7F_{15}$-$^{13}CF_2$—$C^2H$=$C^2H_2$.

Example 6

Perfluoroheptyl Iodide (12.65 g, 25 mmol) in ether (100 mL) was cooled to −50° C. and reacted with 3M solution of ethylmagnesium bromide in ether for 1 h. The reaction mixture was cooled in liquid nitrogen bath, tetrahydrofuran (100 mL) added, and carbon dioxide [$^{14}C$] (1400 mCi, 24 mmol) added by condensing in vacuum. The reaction flask was warmed to −78° C. (over 4 h), and then warmed to room temperature overnight. The reaction mixture was quenched with 6N sulfuric acid at −30° C. and most of the organic solvents removed. The aqueous layer was adjusted to pH 11 with 25% sodium hydroxide, washed with pentane, and acidified to pH 1 with 6N hydrochloric acid. The aqueous layer was extracted with dichloromethane. The organic layer was washed with water, dried over anhydrous sodium sulfate, and concentrated. The residue was distilled under vacuum (60° C./1 Torr) to obtain 1-$^{14}$C-perfluorooctanoic acid (1100 mCi, 19 mmol).

1-$^{14}$C-Perfluorooctanoic acid (1100 mCi, 19 mmol), prepared as above, was vacuum transferred into a flask containing DEOXOFLUOR (8.436 g, 38 mmol) cooled in liquid nitrogen bath. The flask was allowed to warm to room temperature and the product was distilled under vacuum (20° C./1 Torr) to obtain 1-$^{14}$C-perfluorooctanoyl fluoride (3.5 mL, ~14 mmol).

A mixture of anhydrous potassium fluoride (0.33 g, 5.7 mmol), tetraglyme (4.0 mL), hexafluoropropylene oxide (HFPO) (1215 mL, 48 mmol), and 1-$^{14}$C-perfluorooctanoyl fluoride (3.5 mL, ~14 mmol) was heated at 60° C. under vacuum (~1 mm) for 36 h. The product was distilled under vacuum (60° C./1 Torr) and collected at −78° C.

A mixture of $C_7F_{15}{}^{14}CF_2OCF(CF_3)C(O)F$ (~14 mmol) and lithium iodide (3.72 g, 28 mmol) was heated at 90° C. under vacuum (~1 mm) for 3 h. The product ($C_7F_{15}{}^{14}CF_2OCF(CF_3)C(O)I$, 4.2 mL) was distilled in vacuum (60° C./1 Torr) and collected at −20° C.

$C_7F_{15}{}^{14}CF_2OCF(CF_3)C(O)I$ (4.2 mL), prepared as above, was evacuated, closed and heated at 215° C. for 16 h. The product was distilled under vacuum (20° C./1 Torr) and trapped at −20° C. to obtain 1-$^{14}$C perfluorooctyl iodide (1.7 mL), which was used to obtain further derivatives.

Example 7

1-$^{14}$C-perfluorooctyl Iodide (1.7 mL, 1.4 g, 6.2 mmol), as prepared in Example 6, and 1,1,2-trichlorotrifluoroethane (0.5 mL), were charged into a steel vessel (capacity 35 mL). The ethylene was added (372 mL, 14.88 mmol) and the mixture was heated at 200° C. for 15 h. The reaction mixture was transferred under vacuum (1 mmHg) at 80° C., and 1-iodo-3-$^{14}$C-1H,1H,2H,2H-perfluorodecane (200 mCi, 3.4 mmol) was collected at −20° C.

Example 8

A mixture of 1-iodo-3-$^{14}$C-1H,1H,2H,2H-perfluorodecane (200 mCi, 3.4 mmol), prepared as in Example 7, N,N-dimethylformamide (9 mL), and water (0.9 mL) were heated at 120° C. for 20 h. The reaction mixture was diluted with water (50 mL) and extracted with ether. The ether layer was concentrated at about 20 mmHg. The residue was dissolved in 1,1,2-trichlorotrifluoroethane and purified by column chromatography (silica gel, pentane/ether, 3/1, 600 mL). Fractions containing product were combined and concentrated. The residue (57 mCi) was further purified by distillation under vacuum (about 1 mm Hg) at 80° C. and 3-$^{14}$C-1H,1H,2H,2H-perfluorodecan-1-ol was collected at −20° C. (54 mCi, 460 mg). Radiochemical purity: greater than 98.16%, specific activity (weight assay) 54.3 mCi/mmol. Structure confirmed by $^1$H and $^{19}$F NMR (CDCl$_3$).

What is claimed is:

1. A process for the preparation of a compound of $$R_f\text{—}^aCF(U)_y(T)_z \quad\quad \text{Formula 1C}$$

wherein $R_f$ is a linear or branched perfluoroalkyl radical $Z(C_mF_{2m})$—, m is 1, 3 to 20, or a mixture thereof;

Z is F when m is 1 and Z is selected from F, Cl, or H when m is 3 to 20 or a mixture thereof;

a is 13 or 14;

y and z are each 1;

U is F; and

T is —X wherein X is I or Br, comprising a) contacting a perfluoroalkyl metallic compound of formula $$(R_f)_{(v-w)}MX_w$$

wherein $R_f$ is a linear or branched perfluoroalkyl radical $Z(C_mF_{2m})$—,

M is selected from the group consisting of Zn, Cd, Mg, Ca, and amalgams thereof with Hg, X is I or Br, v is the valence of M, and w is 1, with $^aCO_2$ to generate the corresponding acid $R_f$—$^aCOOH$;

b) contacting the acid from step a) with a fluorinating agent to yield $R_f$—$^aC(O)F$;

c) contacting the $R_f$—$^aC(O)F$ with a substituted trifluorooxirane in the presence of a fluoride ion source to yield $R_f$—$^aCF_2$—O—CF[(CF$_2$)$_p$R"]—C(O)F wherein R" is H or F and p is 1 to 8; and d) contacting $R_f$—$^aCF_2$—O—CF[(CF$_2$)$_p$R"]—C(O)F with a metal iodide or metal bromide and heating to yield $$R_f\text{—}^aCF(U)_y(T)_z.$$

2. A process for the preparation of a compound of $$R_f\text{—}^aCF(U)_y(T)_z \quad\quad \text{Formula 1C}$$

wherein $R_f$ is a linear or branched perfluoroalkyl radical $Z(C_mF_{2m})_m$ m is 1, 3 to 20, or a mixture thereof;

Z is F when m is 1 and Z is selected from F, Cl, or H when m is 3 to 20 or a mixture thereof;

a is 13 or 14;

y and z are each 1;

U is F; and

T is —X wherein X is I or Br, comprising a) contacting $(R_f)$—X wherein $R_f$ and X are as defined above with R—Mg—X wherein R is $C_1$-$C_4$ alkyl to yield $R_f$—Mg—X, b) contacting $R_f$—Mg—X with $^aCO_2$ to yield $R_f$—$^aCOOH$, c) contacting the $R_f$—$^aCOOH$ from step b) with N,N-diethylaminosulfur trioxide to yield $R_f$—$^aC(O)F$;

d) contacting the $R_f$—$^aC(O)F$ with hexafluoropropylene oxide in the presence of KF to yield $R_f$—$^aCF_2$—O—CF(CF$_3$)—C(O)F;

e) contacting $R_f$—$^aCF_2$—O—CF(CF$_3$)—C(O)F with a metal iodide or metal bromide to yield $R_f$—$^aCF_2$—O—CF(CF$_3$)—I or $R_f$—$^aCF_2$—O—CF(CF$_3$)Br;

f) heating $R_f$—$^aCF_2$—O—CF(CF$_3$)—I or $R_f$—$^aCF_2$—O—CF(CF$_3$)Br to yield $R_f$—$^aCF_2$—I or $R_f$—$^aCF_2$Br respectively.

* * * * *